United States Patent [19]

Fritzlen et al.

[11] 4,268,751

[45] May 19, 1981

[54] INFRARED BREATH ANALYZER

[75] Inventors: Jack D. Fritzlen, Vail; Fred M. Thul, Avon; Douglas R. Vogel, Vail, all of Colo.

[73] Assignee: CMI Incorporated, Minturn, Colo.

[21] Appl. No.: 25,904

[22] Filed: Apr. 2, 1979

[51] Int. Cl.³ .................................................. G01J 1/00
[52] U.S. Cl. ..................................................... 250/343
[58] Field of Search ................. 250/340, 343, 344, 345

[56] References Cited

U.S. PATENT DOCUMENTS

| | | | |
|---|---|---|---|
| 3,560,736 | 2/1971 | Billetdeaux et al. | 250/343 |
| 3,562,524 | 2/1971 | Moore et al. | 250/343 |
| 3,792,272 | 2/1974 | Harte et al. | 250/343 |
| 4,013,260 | 3/1977 | McClatchie et al. | 250/343 |
| 4,057,724 | 11/1977 | Adrian et al. | 250/343 |

Primary Examiner—Davis L. Willis
Assistant Examiner—Janice A. Howell
Attorney, Agent, or Firm—Sheridan, Ross, Fields & McIntosh

[57] ABSTRACT

A breath analyzer is provided to test for the presence of an unknown infrared energy absorbing compound in a breath sample collected from an individual. Infrared energy of at least two wavelengths is passed through the collected sample. The first wavelength of infrared energy, 3.48 microns for example, is selected to be significantly absorbed by a predetermined infrared energy absorbing compound, such as ethanol. The second wavelength of infrared energy, 3.39 microns for example, is selected to be significantly absorbed by other infrared energy absorbing compounds, such as acetone. The infrared energy remaining in the first wavelength after its passing through the breath sample is compared to the infrared energy remaining in the second wavelength after its passing through the breath sample. The lack of a predetermined comparison value indicates the presence of an infrared energy absorbing compound other than the predetermined infrared energy absorbing compound.

Additionally, the first wavelength of remaining infrared energy is processed to determine the concentration of the predetermined infrared energy absorbing compound present in the breath sample.

22 Claims, 4 Drawing Figures

FIGURE 1
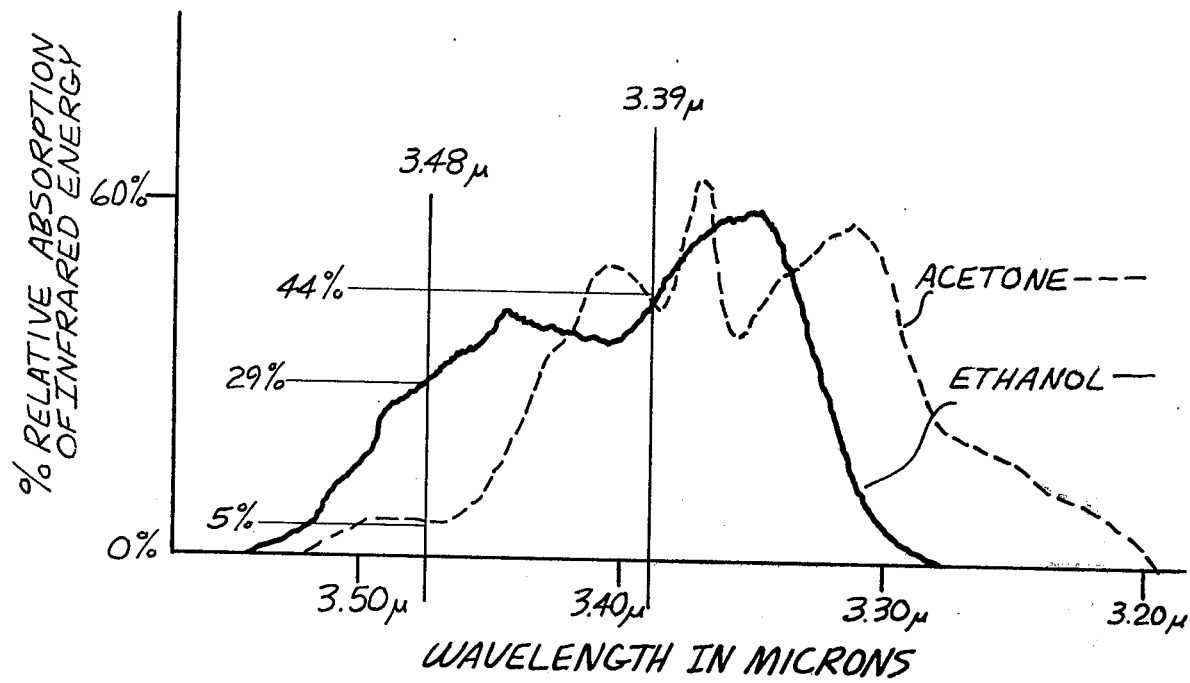
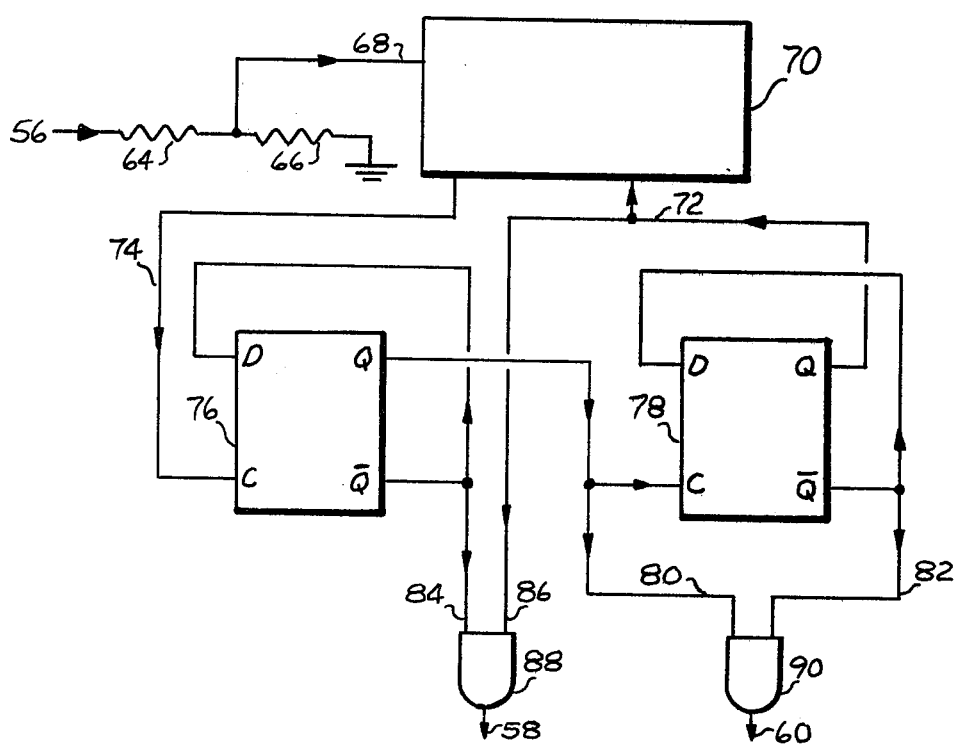
FIGURE 4. TIME WINDOW GENERATOR 32

INFRARED BREATH ANALYZER

DESCRIPTION

1. Technical Field

This invention is in the field of method and apparatus for detecting the presence of an energy absorbing compound in the collected breath sample of a human test subject.

2. Background Art

In the law enforcement area, it is of great value to determine the Blood Alcohol Content (BAC) of subjects suspected of driving while intoxicated where the BAC may be subsequently used as evidence in a related court proceeding. While direct blood analysis is acceptable and widely used, it is expensive and time consuming. For many years it has been known that ethanol (the specific type of alcohol of interest) appears in the breath of an individual in a direct proportion to the individual's BAC. Thus many instruments which measure a breath sample have been designed expressing the test result directly in BAC using the established and legally accepted blood breath correlation factor. Various means including chemical processing, gas chromatography and infrared absorption techniques have been successfully utilized. The infrared technique on which the present invention is based offers many advantages over the others in terms of test simplicity and low cost per test. The principles and practical implementation of the infrared means to measure the ethanol concentration in a sample are well known to those skilled in the art and are fully described in U.S. Pat. No. 3,792,272 issued on Feb. 12, 1974 to Harte, et al. and entitled "Breath Test Device for Organic Compounds, including Alcohol", and U.S. Pat. No. 4,057,724 issued on Nov. 8, 1977 to Adrian, et al. and entitled "Determination of the Alcohol Content of the Blood", so they will not be reiterated here. However, if the infrared measurement is conducted only at a single wavelength of energy (e.g., 3.39 microns) which ethanol strongly absorbs, the quantitation of ethanol will be rendered inaccurate and overstated if other energy absorbing compounds, such as acetone which also absorbs 3.39 microns energy, are present in the breath sample. The present invention provides an apparatus and method to detect the presence of unsuspected energy absorbing compounds (e.g., acetone) in the breath sample so that the expressed results of the test will more fully meet the evidential stature required of the test and thereby accurately reflect the concentration of ethanol in the breath sample.

PRIOR ART STATEMENT

The following references are submitted under the provision 37 CFR 1.97 (b).
U.S. Pat. No. 3,792,272; Harte, et al.
U.S. Pat. No. 4,057,724; Adrian, et al.

Harte, et al., U.S. Pat. No. 3,792,272, discloses a suitable apparatus to detect and quantify breath ethanol content of a collected sample and express that quantity in terms of BAC (Blood Alcohol Content). The Harte, et al. apparatus uses a single infrared wavelength (3.39 microns) which is absorbed by ethanol and other energy absorbing compounds including acetone, a ketone found in trace amounts in the blood and breath of certain diabetics and dieters. One of the primary uses of the Harte, et al. apparatus is for the breath testing of suspected drunk drivers by law enforcement agencies. The inability of the Harte, et al. apparatus to distinguish ethanol from other energy absorbing compounds naturally occurring in the breath (e.g., acetone) or ingested compounds (e.g., turpentine) reduces its stature as legal evidence. Only if the test operator has reason to suspect the presence of these other compounds in the breath of a test subject will a test by other means, such as direct blood test, be made to confirm whether another energy absorbing compound besides ethanol is present. Since the presence of other energy absorbing compounds may go unsuspected, the possibility of such a presence in the breath sample can be subsequently raised by any person on which a confirming test was not accomplished. Of course to do the confirming test in each case would solve the problem, but then the speed, low cost and other advantages of a breath test by infrared means would be defeated. Harte, et al. further discloses the basic physical principles involved in quantitative measurement of ethanol and other compounds using infrared absorption on which the present invention is based. Harte, et al. further discloses rather completely a suitably packaged and error-detecting apparatus for use outside of the laboratory environment such as in a police station.

Adrian, et al, U.S. Pat. No. 4,057,724, discloses a breath test device similar to Harte, et al. and intended primarily for the same usage. Adrian, et al. reiterates and expands the underlying principles of infrared measurement techniques for breath tests. Adrian, et al. particularly points out that while the absorption bands of ethanol and acetone overlap, their absorption amounts differ relatively at discrete wavelengths within a band (e.g., 3.39 microns as compared to 3.48 microns). This principle is also fundamental to the present invention. Adrian, et al. also notes the problem of acetone naturally appearing in the breath of certain individuals and provides an exchangeable optical filter by which a subsequent confirming test may be accomplished if the test operator suspects the presence of acetone. Adrian, et al. does not address the problem of ingested volatile substances (e.g., turpentine).

DISCLOSURE OF THE INVENTION

The present invention provides both method and apparatus for detecting the possible presence of an energy absorbing compound in a breath sample which may render inaccurate a measurement of the concentration of a predetermined energy absorbing compound, such as ethanol, present in the sample. Two predetermined wavelengths of infrared energy are applied to the same breath sample contained in a chamber, either alternately or simultaneously, at least one of which wavelengths is sufficiently absorbed by ethanol or another predetermined energy absorbing compound for measurement purposes. Obviously a compound not absorbing either wavelength will not affect the test at all but, if it is absorbing the energy of the second wavelength, its presence can be detected as will be more fully explained later. The infrared energy remaining in each of the two wavelengths after absorption by the collected sample is received by an infrared detector which converts this remaining quantity of infrared energy to an equivalent electrical signal. The energy remaining from each wavelength is kept separate for measurement purposes.

Prior to the collection of actual breath samples, values are obtained for the energy remaining in each wavelength after its absorption by ethanol. These values are established by introducing ethanol concentrations known to be free of other energy absorbing compounds into the collection chamber and recording the results. The difference in the energy remaining between the two predetermined wavelengths can then be found. This same procedure could be used with any other energy absorbing compound if it is desirable to determine its concentration in a sample while assuring that no other compound is absorbing the energy of the predetermined wavelengths.

In contrast to other energy absorbing compounds, the value representing the difference in the energy remaining in the two predetermined wavelengths after absorption by ethanol will be unique for any anticipated ethanol concentration to be tested. To simplify the present invention, the wavelength whose absorption by ethanol is greater is optically and/or electronically attenuated to be equal to the wavelength of lesser ethanol absorption so that the energy absorption of both wavelengths is made equal for any concentration of ethanol. Thus a predetermined value representative of the difference between the two infrared wavelengths is conveniently made equal to zero when ethanol is the only energy absorbing compound present in the sample. During the test, the energy levels of both wavelengths are continuously compared and their difference is required to remain substantially constant at the predetermined value of zero throughout the test. Otherwise, the presence of an energy absorbing compound other than ethanol is detected.

It is therefore the object of this invention to provide method and apparatus for detecting the presence of an energy absorbing compound other than a predetermined compound, such as ethanol, in a collected breath sample.

BRIEF DESCRIPTION OF DRAWINGS

Other objects, features and advantages of the invention will be readily apparent from the following description of certain preferred embodiments taken in conjunction with the accompanying drawings, although variation and modification may be affected without departing from the spirit and scope of the novel concepts of the disclosure in which:

FIG. 1 is a plot of the relative absorption of infrared energy by ethanol and acetone in the 3.39 micron region;

FIG. 4 is a detailed schematic of the time window generator of FIG. 2.

BEST MODE FOR CARRYING OUT THE INVENTION

FIG. 1 depicts the relative absorption response of ethanol and acetone in the 3.39 micron region and the specific two wavelengths, 3.39 and 3.48 microns, used in the preferred embodiment are marked. It will be noted that the relative percentage or concentration of infrared energy absorbed by acetone is approximately equal to the concentration of ethanol absorbed at 3.39 microns while the relative concentration of infrared energy absorbed by acetone at 3.48 microns is less than that absorbed by ethanol at 3.48 microns. Acetone is selected for example purposes because in some cases it can naturally occur in the human breath and this is of particular interest. Usually, other compounds are present in significant amounts only if ingested, but will be detected as well. They may have absorbed energy in the 3.39 micron region, but each will exhibit a characteristic response different from ethanol, and for that matter acetone, as depicted in FIG. 1. The difference in the response is due to the fact that different infrared energy absorbing compounds do not absorb the same percentage or concentration of infrared energy for each discrete wavelength in the 3.39 micron region. Consequently, at least two predetermined wavelengths can be selected such that the difference in the infrared energy remaining between the two predetermined wavelengths after absorption is different for any infrared energy absorbing compound.

Figure 2:
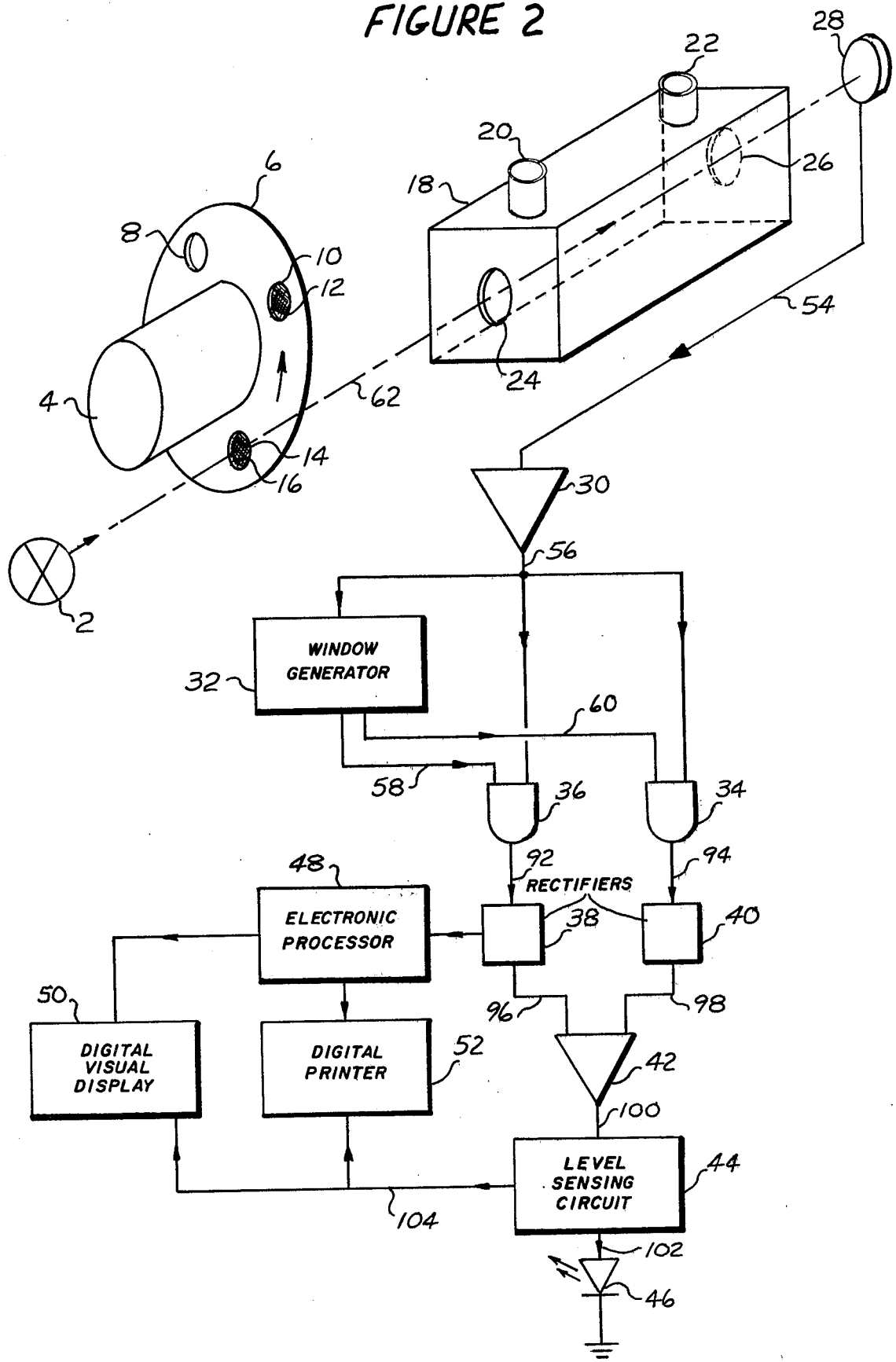
FIG. 2 is a combination block and schematic diagram of the present invention.

FIG. 2 depicts the apparatus of the present invention schematically. A suitable power supply furnishing regulated DC power to infrared source 2, motor 4, and the electronic circuits is provided but not shown. The apparatus includes the board banded infrared source of energy 2, such as an incandescent lamp, mounted therein. Those skilled in the art will know that many alternate infrared sources ranging from lasers to heater wires can be provided. The terms broad band and narrow band will be used in this disclosure when describing an infrared source of energy, optical filters, and an infrared detector of energy. By broad band is meant the presence of many discrete wavelengths of energy analagous to the situation where white light is the broad banded composite of many discrete wavelengths seen by the eye as individual colors. A narrow band of energy, on the other hand, contains only a single (or closely grouped) wavelength. A portion of the source of energy, hereinafter referred to as the beam 62, will pass through elements of the apparatus usefully terminating at the infrared detector 28. The beam is first interrupted by a filter wheel 6, driven by a motor 4, which is opaque to the beam 62 except for three apertures. One aperture 8 is totally open and passes all wavelengths generated by the source 2. The second aperture 10 is covered by a narrow band 3.39 micron optical filter 12 and the third aperture 14 by a narrow band 3.48 micron optical filter 16. In the preferred embodiment, it is desired to equalize the absorption response of ethanol at both 3.39 microns and 3.48 microns. This can be accomplished by optically attenuating the 3.39 wavelength of energy by reducing the size of the aperture 10 covered by the 3.39 micron filter 12 with respect to the aperture 14 covered by the 3.48 micron filter 16. Alternatively, it is readily appreciated that an embodiment may be provided in which the difference in energy absorption for the two wavelengths is other than zero provided that this difference is known. It is not necessary then that the difference in energy absorbed by a predetermined compound from two predetermined, different wavelengths of energy be equal to zero. Rather, it is only necessary that there be a difference in the energy absorption between energy absorbing compounds for the two different wavelengths. Consequently, the difference in energy absorption for the two different wavelengths can be compared with the known or expected difference. If the expected difference is present only the predetermined compound, such as ethanol, is present. Otherwise some other energy absorbing compound is present.

Because of the spaced apertures 8, 10, 14 formed in rotating filter wheel 6, the beam downstream from the filter wheel 6 is no longer continuous but a recurring succession of timewise separated pulses of infrared energy, and consists of a first pulse of broad banded infrared energy followed by a second pulse of narrow band 3.39 microns infrared energy and in turn followed by a third pulse of narrow band 3.48 microns infrared energy. This pulsed beam 62 continues through the breath sample chamber 18 by means of quartz windows 24, 26 at each end. The chamber 18 is also equipped with appropriate inlet 20 and outlet 22 to introduce, store, and purge the breath sample to be tested. While the inlet 20 and outlet 22 may be closed after the proper breath sample is collected in the chamber 18, it is not necessary. It is only necessary that the beam 62 pass through the breath sample. Also the breath sample need not be directly collected, but could be introduced from a previously stored sample. The present invention can also be applied to any gaseous compound other than human breath samples. After leaving the chamber 18 the beam impinges on an infrared detector 28 whose output 54 is an electrical signal proportional to the amount of infrared energy remaining in the impinging beam. The infrared detector 28 is typically a lead sulphide photocell of the photoresistive type. It is understood that two infrared detectors could be provided rather than a single infrared detector. Each infrared detector would sense the energy remaining in only one of the predetermined wavelengths in order to separate the electrical signals representing the remaining energy. After amplification by amplifier 30 to suitable circuit operating levels, this amplified electrical signal 56 is first directed to a time window generator circuit 32. By selecting the proper size for aperture 8 the broad banded energy pulse can be predictably made to always generate an electrical output greater in amplitude than the other two pulses filtered through apertures 10, 14. The broad banded pulse is therefore electronically identified and separated by its greater amplitude.

FIGS. 3A–3K illustrate the time-related occurrence of input and output signals at selected points in the energy detecting and comparing circuitry of this invention. Time is conveniently expressed on the horizontal axes in degrees of filter wheel rotation which is a function of motor 4 speed (revolutions/minute) while the vertical axes represnet the relative percentage of energy remaining in the wavelengths after their passing through the collected sample.

Figure 3:
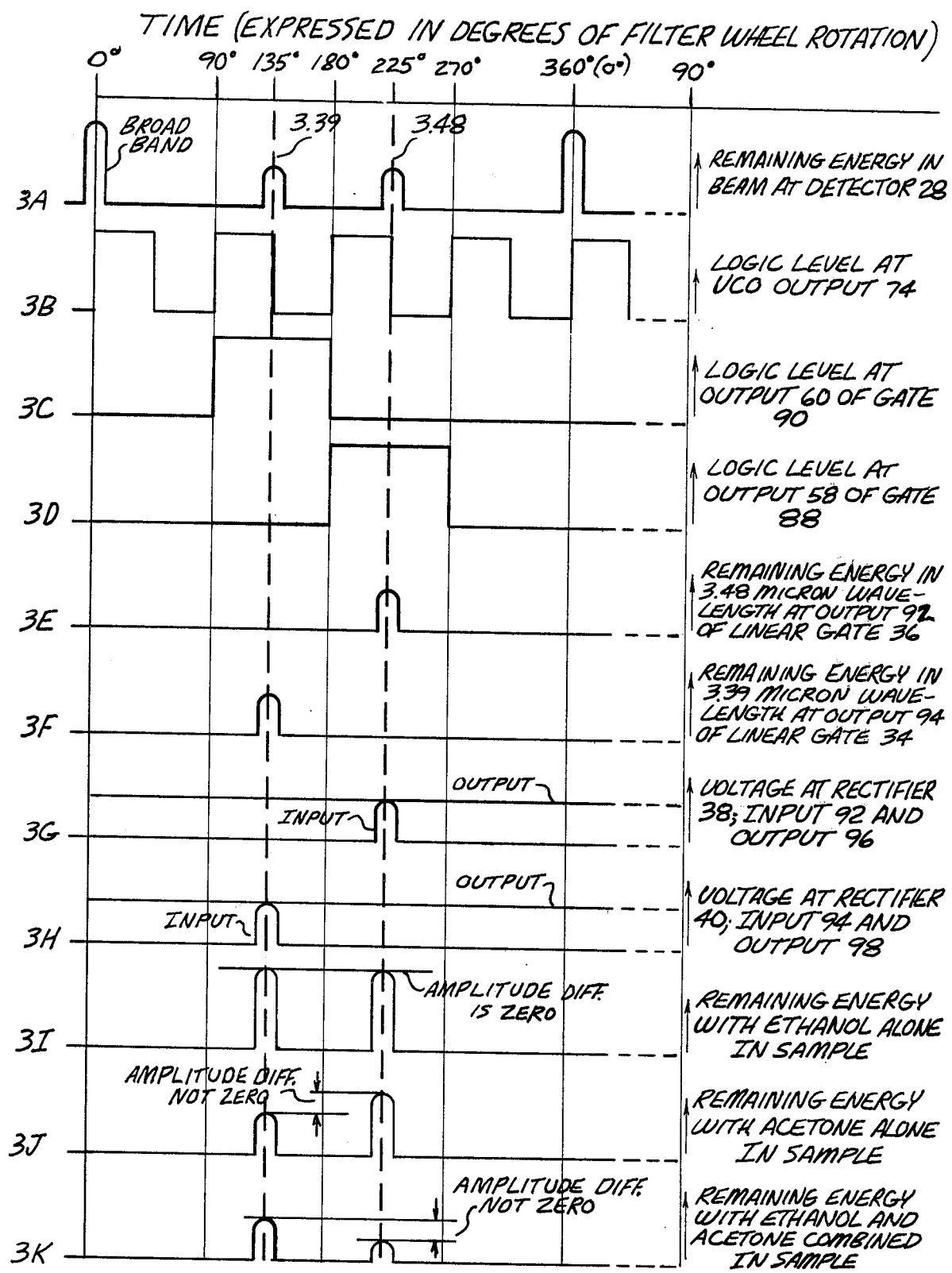
FIG. 3 is a time relationship diagram of the infrared energy pulses at selected circuit outputs.

In FIG. 3A the filtered pulses of beam 62 are illustrated after their amplification by amplifier 30 with the timewise appearance thereof related to the spacing of the apertures 8, 10, 14 of filter wheel 6. Breaking the filter wheel 6 into a spacing of 360 degrees, the aperture 8 is considered to be at 0 degrees. Aperture 10 is spaced at 135 degrees and aperture 14 at 225 degrees. FIG. 3A also depicts the output 56 of the amplifier 30 when a concentration of ethanol is present in the sample with virtually no other energy absorbing substance present. It is understood that if other energy absorbing compounds are present in the sample at least one of the output pulses of detector 28 has an amplitude different than the amplitude of pulses depicted in FIG. 3A. In FIG. 4, which is a detailed schematic of time window generator 32, output 56 is first applied to an attenuator consisting of two resistors 64, 66 so that only the broad banded energy pulse remains strong enough at the input 68 of the phase lock loop 70 to be detected and control the input 68 of the phase lock loop 70. The phase lock loop 70 is integrated circuit type 4046 manufactured by RCA Corp. of New York, N.Y. Only the significant portions of the necessary circuit are depicted in FIG. 4.

For a full understanding of Phase Lock Loop principles and the means to select proper valued components to fully implement the 4046 in the present invention reference is made here to the Application note ICAN 6101 in the SSD-203C 1975 Databook series published by RCA Corporation. In FIG. 4, the VCO output 74 has its frequency divided by four by means of two Type D flip flops 76, 78 as shown. The implementation of Type D flip flops and their arrangement to divide by four a given input frequency is well known to those skilled in the art. This divided output 72 appearing at Output Q of flip flop 78 is applied to Input 2 of the phase lock loop comparator. Phase-Comparator II circuitry of the phase lock loop type 4046 is employed. Noted here is the ability of the phase lock loop 70 to track a wide range of frequencies applied at its input 68 so the motor 4 speed need not be precisely controlled. The phase lock loop 70 will operate to synchronize the leading edge of the broad band energy pulse at 68 with every fourth pulse of the VCO output 74. This timewise relationship is depicted in FIG. 3B. Gates 88, 90 when connected as shown will produce pulses (time windows) at their respective outputs 58, 60 as shown in FIGS. 3D and 3C. With the generation of the time windows 58, 60 the description of the time window generator 32 is complete and attention is drawn back to FIG. 2. The time window output 58 controls a linear AND gate 36 whose other input 56 comprises an electrical signal which includes all three infrared pulses, namely, the pulses representing the energy remaining in the broad band wavelength, the 3.39 micron wavelength and the 3.48 micron wavelength after their passing through the sample. The AND gate 36 outputs a signal representing the energy remaining in the 3.48 micron wavelength when the time window output 58 and the 3.48 infrared pulse occur simultaneously. Similarly, the AND gate 34 outputs a signal representing the energy remaining in the 3.39 micron wavelength when the time window output 60 and the 3.39 infrared pulse occur simultaneously. The output 92 of gate 36 is depicted by FIG. 3E and illustrates the infrared energy remaining in the 3.48 wavelength completely separated from the pulse of FIG. 3F which represents the energy remaining in the 3.39 wavelength at output 94 of gate 34. Thus, it can be appreciated that the separate pulses representing the energy remaining in the 3.48 and 3.39 wavelengths can be compared.

Those skilled in the art will know the many alternate means to generate and keep separate two wavelengths of infrared energy and the means to separately measure their remaining energy content after their passing through a collected breath sample. The filter wheel 6 if placed in the beam 62 after it has passed through the sample, would work equally well. Alternatively, the broad band source 2 could be replaced by two narrow band sources selected at the proper wavelengths. Another alternative would be to use two narrow band detectors in combination with a broad band source. What is essential to the present invention is that the collected sample be subjected to at least two wavelengths of energy and to separately measure the amount of remaining energy remaining at each wavelength after absorption by the sample. Obviously, more than two wavelengths of energy could be used to quantitate a second predetermined energy absorbing compound or to qualitate the unknown energy absorbing compounds.

Downstream from the two AND gates 36, 34 conventional rectifiers 38, 40, which further process the separated and hereinafter referred to as the 3.39 and 3.48 channels, are essentially identical circuits so that the equality of the energy remaining in both wavelengths is electrically preserved. The phase pulses at the outputs 92, 94 of the two AND gates 36, 34 are applied to rectifiers 38, 40 to convert their amplitude content which is essentially AC form to a DC form whose DC voltage is proportional to the amount of energy remaining in the 3.39 and 3.48 wavelengths after their passing through the breath sample. This rectification is necessary because the pulses appearing at gate outputs 92 and 94 do not occur at the same time and cannot be directly compared. FIG. 3G and 3H depict the DC voltage at rectifier inputs 92 and 94 and outputs 96 and 98 whose DC voltage amplitude is proportional to the peak amplitude of the pulses appearing at the rectifier inputs 92 and 94 depicted in FIG. 3E and 3F. It is seen that the continuous or DC outputs 96 and 98 occur simultaneously. Each of the outputs 96, 98 of each rectifier 38, 40 is delivered to one of the two inputs of a differential amplifier 42 whose output or comparison value will be equal to the predetermined value of zero if its two inputs remain equal. As previously described, if the amount of energy absorption of each wavelength had not been equalized by adjusting the size of aperture 10, the predetermined value would be other than zero but this value would still be known and unique for each predetermined energy absorbing compound, such as ethanol. Consequently, this known and unique predetermined value can be compared with the output or comparison value 100 of differential amplifier 42. If the predetermined value and the output of differential amplifier 42 do not properly compare, the presence of an energy absorbing substance other than ethanol, such as acetone, has been detected. An understanding of why this is so is appropriate here.

FIGS. 3I-3K depict the remaining energy of each predetermined wavelength after its passing through the chamber 18 when various known concentrations of ethanol and acetone alone and in combination are introduced into the collection chamber 18. FIG. 3I is similar to FIG. 3A with the broad banded energy pulse removed and assumes ethanol alone present in the sample being analyzed. FIG. 3J depicts the presence of acetone alone in the sample being analyzed. FIG. 3K depicts the energy remaining in the two wavelengths, 3.48 and 3.39 microns, when the concentrations depicted in FIGS. 3I and 3J are assumed. It is the amplitude of these pulses, which is representative of the energy remaining in the wavelengths, that is separately recitified and applied at the inputs 96, 98 of the difference amplifier 100. Thus, if the amplitudes as depicted in FIG. 3I are equal as they are in the case of ethanol alone, then the recitifier outputs 96, 98 are equal and the difference amplifier 42 output 100 is zero. FIG. 3J shows the relative unequal amplitudes when acetone alone is present. This inequality results since the energy remaining in the 3.39 wavelength is less than the energy remaining in the 3.48 wavelength inasmuch as more energy of the 3.39 wavelength is absorbed by the acetone than the energy in the 3.48 wavelength. This inequality now appears at the inputs 96, 98 of the difference amplifier 42 whose output 100 will be other than zero. To complete the illustration, FIG. 3K depicts the presence of both ethanol and acetone in the sample. Since the energy reamining in the acetone is unequal for the two different wavelengths, the amplitudes representing the ethanol and acetone combination remain unequal so the output 100 is other than zero. A conventional level sensing circuit 44 which provides the means for comparing the predetermined value of zero with the output 100 of differential amplifier 42, detects this not zero condition and delivers an output 102 which turns on an indicator 46, such as a light emitting diode. Indicator 46 provides either an audible or visual indication that an energy absorbing compound other than ethanol is present in the sample. Optionally, another output 104 of the not zero sense circuit 44 could inhibit the display 50 or print 52 of the test results.

The balance of means necessary to implement this invention into a practical breath test apparatus is well known. The rectified DC output 96 of rectifier 38 has an electrical value proportional to the amount of ethanol in the collected breath sample provided another energy absorbing compound is not also present. The electronic processor 48 converts this electrical value to digital form, scaled to Blood Alcohol Content (BAC) or any other desired scale. The output of the electronic processor in turn will drive a Digital Visual Display of BAC 50 such as seven segment light emitting diodes and/or a Digital Printer of BAC 52.

From the foregoing, it should be evident that various modifications can be made to the described embodiments without departing from the scope of the present invention.

We claim:

1. An apparatus to determine the presence, in a sample, of an unknown energy absorbing compound when a predetermined energy absorbing compound is also present in the sample and where both the unknown energy absorbing compound and the predetermined energy absorbing compound both absorb first and second predetermined wavelengths of energy, comprising:
   generating means for producing said first predetermined wavelength of energy and said second predetermined wavelength of energy, both said first predetermined wavelength and said second predetermined wavelength being absorbed by both the unknown energy absorbing compound and the predetermined energy absorbing compound when both compounds are present in the sample;
   chamber means in the path of said first and second predetermined wavelengths of energy for receiving the sample and for passing said first and second predetermined wavelengths therethrough;
   detecting means in the path of said first and second predetermined wavelengths for sensing separately the amount of energy remaining in each of said first and second predetermined wavelengths after the passing of said first and second predetermined wavelengths through said chamber means; and
   comparing means connected to said detecting means for comparing the amount of energy remaining in said first predetermined wavelength with the amount of energy remaining in said second predetermined wavelength, said comparing means outputting a comparison value, the comparison value being known and unique for the predetermined energy absorbing compound so that, if the comparison value outputted is different than the known and unique comparison value for the predetermined energy absorbing compound, an unknown energy absorbing compound is present in said chamber means.

2. The apparatus, as claimed in claim 1, further including:

indicating means connected to said comparing means for signaling an improper comparison between said first and second predetermined wavelengths of energy thereby indicating that an energy absorbing compound other than the predetermined energy absorbing compound is present in said chamber means.

3. The apparatus, as claimed in claim 1, wherein said comparing means includes:
difference means connected to said detecting means for obtaining the difference in the amount of energy remaining between said first and second predetermined wavelengths of energy;
means connected to said difference means for providing a predetermined value to compare the difference obtained by said difference means with the predetermined value to determine the presence of an energy absorbing compound other than the predetermined energy absorbing compound.

4. The apparatus, as claimed in claim 3, wherein:
the predetermined value is unique for the predetermined energy absorbing compound so that the presence of an energy absorbing compound other than the predetermined energy absorbing compound is found when the difference in the amount of remaining energy between said first and second predetermined wavelengths is different than the predetermined value.

5. The apparatus, as claimed in claim 1, wherein said generating means includes:
an infrared energy source producing a broad band of wavelengths; and
at least one narrow band optical filter for passing only one of said first and second predetermined wavelengths.

6. The apparatus, as claimed in claim 1, wherein said generating means includes:
a first narrow band infrared energy source which outputs a wavelength equal to said first predetermined wavelength; and
a second narrow band infrared energy source which outputs a wavelength equal to said second predetermined wavelength.

7. The apparatus, as claimed in claim 1, wherein said detecting means includes:
at least a first infrared energy detector to sense only infrared energy remaining in said first predetermined wavelength after its passing through said chamber means; and
at least a second infrared energy detector to sense only infrared energy remaining in said second predetermined wavelength after its passing through said chamber means.

8. The apparatus, as claimed in claim 1, wherein:
said detecting means includes a single infrared energy detector to sense infrared energy remaining in said first and second predetermined wavelengths after their passing through said chamber means.

9. The apparatus, as claimed in claim 1, wherein:
said detecting means includes rectifying means connected to said comparing means for coverting electrical signals representing the amount of energy remaining in said first and second predetermined wavelengths into substantially continuous signals proportional to the electrical signals inputted thereto so that the amount of energy remaining in said first and second predetermined wavelengths can be compared by said comparing means.

10. The apparatus, as claimed in claim 9, wherein said rectifying means includes:
a first rectifier to receive only the electrical signal representing the energy remaining in said first predetermined wavelength; and
a second rectifier to receive only the electrical signal representing the energy remaining in said second predetermined wavelength.

11. The apparatus, as claimed in claim 10, wherein said detecting means further includes:
timing means connected to said rectifying means for enabling the electrical signal representing the energy remaining in said first predetermined wavelength to be applied only to said first rectifier and for enabling the electrical signal representing the energy remaining in said second predetermined wavelength to be applied only to said second rectifier.

12. The apparatus, as claimed in claim 1, wherein:
the predetermined energy absorbing compound is ethanol.

13. The apparatus, as claimed in claim 1, wherein:
said first predetermined wavelength is 3.48 microns and said second predetermined wavelength is 3.39 microns.

14. An apparatus to determine the presence quantitatively of a predetermined infrared energy absorbing compound and concurrently test for the presence of an unknown infrared energy absorbing compound in a sample, said apparatus comprising:
generating means for producing a first predetermined wavelength of infrared energy and a second predetermined wavelength of infrared energy, both said first predetermined wavelength and said second predetermined wavelength being absorbed by both the predetermined energy absorbing compound and the unknown energy absorbing compound when both compounds are present in the sample;
chamber means in the path of said first and second predetermined wavelengths for receiving the sample and for passing said first and second predetermined wavelengths therethrough;
detecting means in the path of said first and second predetermined wavelengths for sensing separately the amount of infrared energy remaining in each of said first and second predetermined wavelengths after the passing of said first and second predetermined wavelengths through said chamber means;
comparing means connected to said detecting means for comparing the amount of energy remaining in said first predetermined wavelength with the amount of energy remaining in said second predetermined wavelength, said comparing means outputting a comparison value, the comparison value being known and unique for the predetermined energy absorbing compound so that, if the comparison value outputted is different than the known and unique comparison value for the predetermined energy absorbing compound, an unknown infrared energy absorbing compound is present in said chamber means; and
processing means connected to said detecting means for converting the amount of infrared energy remaining in one of said first and second predetermined wavelengths of infrared energy to a signal proportional to the concentration of the predetermined infrared energy absorbing compound in the sample.

15. The apparatus, as claimed in claim 14, further including:
  indicating means connected to said comparing means for signaling an improper comparison between said first and second predetermined wavelengths of infrared energy thereby indicating that an infrared energy absorbing compound other than the predetermined infrared energy absorbing compound is present in said chamber means.

16. The apparatus, as claimed in claim 14, further including:
  displaying means connected to said processing means for indicating the concentration of the predetermined infrared energy absorbing compound in the sample.

17. The apparatus, as claimed in claim 14, wherein:
  the predetermined infrared energy absorbing compound is ethanol.

18. A method for determining the presence, in a sample, of an unknown energy absorbing compound when a predetermined energy absorbing compound is also present in the sample and where both the unknown energy absorbing compound and the predetermined energy absorbing compound absorb both first and second predetermined wavelengths of energy, comprising the steps of:
  generating a first predetermined wavelength of energy and a second predetermined wavelength of energy;
  passing said first and second predetermined wavelengths of energy through the sample;
  detecting separately the energy remaining in each of said first and second predetermined wavelengths of energy after their passing through the sample;
  comparing the energy remaining in said first predetermined wavelength with the energy remaining in said second predetermined wavelength to determine whether an unknown energy absorbing compound is present in the sample; and
  outputting a comparison value, the comparison value being known and unique for the predetermined energy absorbing compound so that, if the comparison value outputted is different than the known and unique comparison value for the predetermined energy absorbing compound, an unknown energy absorbing compound is present in the sample.

19. The method, as claimed in claim 18, further including the step of:
  signaling when an improper comparison results between said first and second predetermined wavelengths of energy thereby indicating that an energy absorbing compound other than the predetermined energy absorbing compound is present in the sample.

20. The method, as claimed in claim 18, further including the step of:
  processing the energy remaining in one of said first and second predetermined wavelengths of energy after the passing of said first and second predetermined wavelengths of energy through the sample to determine the concentration of the predetermined energy absorbing compound present in the sample.

21. The method as claimed in claim 18, wherein:
  the predetermined energy absorbing compound is ethanol.

22. The method, as claimed in claim 18, wherein:
  said first predetermined wavelength is 3.48 microns and said second predetermined wavelength is 3.39 microns.

* * * * *